(12) United States Patent
Forsell

(10) Patent No.: US 7,371,208 B2
(45) Date of Patent: May 13, 2008

(54) CAREFUL INCONTINENCE TREATMENT APPARATUS

(75) Inventor: Peter Forsell, Zug (CH)

(73) Assignee: Potencia Medical AG, Baar (CH)

( * ) Notice: Subject to any disclaimer, the term of this patent is extended or adjusted under 35 U.S.C. 154(b) by 0 days.

(21) Appl. No.: 10/543,684

(22) PCT Filed: Jan. 31, 2003

(86) PCT No.: PCT/SE03/00171

§ 371 (c)(1),
(2), (4) Date: Jul. 28, 2005

(87) PCT Pub. No.: WO2004/066886

PCT Pub. Date: Aug. 12, 2004

(65) Prior Publication Data

US 2006/0167337 A1   Jul. 27, 2006

(51) Int. Cl.
*A61F 2/02* (2006.01)
(52) U.S. Cl. ....................................... 600/31
(58) Field of Classification Search ............ 600/29–31, 600/37; 604/327–330, 332, 349, 383, 123
See application file for complete search history.

(56) References Cited

U.S. PATENT DOCUMENTS

| 4,756,949 A | 7/1988 | Spence et al. |
| 4,982,731 A | 1/1991 | Lue et al. |
| 6,067,991 A * | 5/2000 | Forsell ........................ 128/899 |
| 6,319,191 B1 * | 11/2001 | Sayet et al. .................... 600/29 |
| 6,638,208 B1 * | 10/2003 | Natarajan et al. ............. 600/30 |
| 2004/0177918 A1 * | 9/2004 | Murata et al. ............... 156/236 |

FOREIGN PATENT DOCUMENTS

| WO | 00/15158 | 3/2000 |
| WO | 01/47431 | 7/2001 |
| WO | 01/47435 | 7/2001 |

* cited by examiner

*Primary Examiner*—Charles A. Marmor, II
*Assistant Examiner*—Christine D Hopkins
(74) *Attorney, Agent, or Firm*—Nixon & Vanderhye P.C.

(57) ABSTRACT

An apparatus for treating an anal or urinary incontinent patient includes a constriction device is applied on the patient's large intestine or urethra. The constriction device includes an elongate adjustable constriction member extending in a loop around and consisting the large intestine or urethra. An adjustment device adjusts the longitudinal extension of the constriction member in the loop to close the intestinal or urethral lumen and release the large intestine or urethra to open the intestinal or urethral lumen. A layer of a soft viscoelastic material extends between the constriction device and the patient's large intestine or urethra to protect the large intestine or urethra from being eroded by the constriction device. The soft layer has an inwardly directed radial extension in the loop such that when the adjustment device is operated to decrease the longitudinal extension of the constriction member, the layer is forced to expand radially inwardly in the loop causing a corresponding decrease in the cross-sectional area of the intestinal or urethal lumen.

14 Claims, 2 Drawing Sheets

CAREFUL INCONTINENCE TREATMENT APPARATUS

This application is the US national phase of International Application No. PCT/SE2003/000171 filed 31 Jan. 2003, which designated the U.S., the entire content of which is incorporated herein by reference.

The present invention relates to an apparatus for treating an anal or urinary incontinent patient comprising a constriction device adapted to be applied on the patient's large intestine or urethra, the constriction device including an elongate adjustable constriction member adapted to extend in a loop around and constrict the large intestine or urethra, an adjustment device that adjusts the longitudinal extension of the constriction member in said loop to close the intestinal or urethral lumen and release the large intestine or urethra to open the intestinal or urethral lumen, and a layer of a soft material applied on the constriction device. The term "patient" includes an animal or a human being. The term "large intestine" includes the colon, rectum and anal canal.

Anal incontinence is a widespread disease. Several kinds of sphincter plastic surgery are used today to remedy anal incontinence. There is a prior manually operated sphincter system in an initial clinical trial phase where a hydraulic sphincter system connected to an elastic reservoir (balloon) placed in the scrotum is developed. A disadvantage of this system is that thick, hard fibrosis is created around the reservoir by pump movements making the system useless sooner or later.

U.S. Pat. No. 5,593,443 discloses a hydraulic anal sphincter under both reflex and voluntary control. A pressure controlled inflatable artificial sphincter is disclosed in U.S. Pat. No. 4,222,377. WO 01/45488 discloses a hydraulically adjustable constriction device for constricting the large intestine of an anal incontinent patient.

Also urinary incontinence is a widespread problem. Many people are helped through training of the muscles in the pelvic floor but too many have severe problems with urine leakage. Many different solutions to this problem have been tried. For example, there is a prior manually operated urine incontinence treatment apparatus having an artificial hydraulic sphincter device engaging the urethra and connected to an elastic reservoir implanted in the scrotum or in the region of the labia major. A disadvantage of this prior apparatus is that over time hard fibrosis is developed around the reservoir, which may cause malfunction of pumping components. Furthermore, it is a rather complicated task to manually squeeze the elastic implanted reservoir to pump hydraulic fluid to open the sphincter device when the patient needs to urinate. In particular women can get their fingers wet. The created fibrosis will sooner or later become a hard fibroid layer, which may make it even more difficult to pump the reservoir. Yet a further disadvantage is that the use of hydraulic fluid always entails a risk of fluid leaking from implanted hydraulic components.

A prior hydraulic apparatus designed to constrict the urethra is disclosed in U.S. Pat. No. 5,520,606. A prosthetic sphincter with an inflatable cuff, which surrounds the urethra or encloses it on two sides, is disclosed in for example U.S. Pat. Nos. 4,571,749 and 4,222,377. U.S. Pat. No. 4,969,474 discloses a hydraulic method for treating both men and women with urinary incontinence problems in the same way. The apparatus of U.S. Pat. No. 4,969,474 includes a reservoir containing fluid and an inflatable compression means designed to constrict the urethra without risking tissue loss or necrosis to occur. An artificial hydraulically operated urethra sphincter employing an external magnet to achieve closure of the urethra cuff is disclosed in U.S. Pat. No. 5,562,598. WO 01/45488 discloses a hydraulically adjustable constriction device for constricting the urethra of a urinary incontinent patient.

In most of the above-noted prior adjustable devices for treating anal or urinary incontinence, there are an adjustment device that typically comprises an inflatable cavity in the elongate constriction member and hydraulic means for adding hydraulic fluid to and withdrawing hydraulic fluid from the inflatable cavity. In practice, the elongate constriction member is made of silicone, which is a material approved for implantation, and the hydraulic fluid is a liquid such as an isotonic salt solution mixed with other conventional materials.

Since the salt solution is an incompressible liquid the pressure will be the same in the entire cavity of the prior constriction member. In consequence, the entire constriction member will press relatively hard against the intestine or urethra when salt solution is added to constrict the intestine or urethra, which may be injurious to the intestine or urethra.

The object of the present invention is to provide a new incontinence treatment apparatus, which is designed to carefully constrict the patient's large intestine or urethra daily without risking injuring the large intestine or urethra in the long run.

This object are achieved by an apparatus of the kind described initially characterised in that the layer is made of a viscoelastic material and is applied on the constriction device such that it is located between the constriction device and the patient's large intestine or urethra at least along a portion of the constriction member, when the constriction device is implanted, to protect the large intestine or urethra from being eroded by the constriction device, and that the layer of viscoelastic material has an inwardly directed radial extension in said loop such that when the adjustment device is operated to decrease the longitudinal extension of the constriction member, the layer of viscoelastic material is forced to expand radially inwardly in said loop causing a corresponding decrease in the cross-sectional area of the intestinal or urethral lumen.

This results in the important advantage that it is not the constriction member itself, usually made of a relatively hard silicone material, that directly abuts and presses against the large intestine or urethra. Rather, it is the layer of viscoelastic material that carefully abuts and presses against the large intestine or urethra as it is expanded in the loop.

Another important advantage achieved by the present invention is that, depending on the thickness of the layer of viscoelastic material, a relatively small change in the longitudinal extension of the constriction member made by the adjustment device may result in a relatively large change in the restriction of the intestinal or urethral lumen.

For example, the viscoelastic material may comprise a foam or gel of polymer.

Advantageously, the layer of viscoelastic material may completely cover the elongate constriction member and be divided into a series of separate elongate cells of viscoelastic material distributed around the elongate constriction member. As a result, the viscoelastic material located on the inner side of the loop formed by the elongate constriction member is prevented from flowing to the outer side of said loop when the constriction device is adjusted to constrict the large intestine or urethra.

Generally, the adjustment device comprises a powered adjustment device, for example including a motor, preferably an electric motor. The apparatus may comprise an implantable energy-transforming device adapted to transform wireless energy emitted from outside the patient's body into an energy form suited for powering the adjustment device. Such an energy form may be electric energy for powering an electric motor of the adjustment device.

To conveniently adjust the constriction device the apparatus may comprise a wireless remote control for controlling the adjustment device from outside the patient's body.

In accordance with an embodiment of the invention the constriction member comprises a hydraulic constriction member, typically with an inflatable cavity, and the adjustment device comprises a pump hydraulically connected to the hydraulic constriction device.

In a preferred simple mechanical embodiment of the invention, the constriction member is non-inflatable and comprises a main portion and two elongated end portions. The adjustment device is adapted to establish longitudinal relative displacement between the end portions of the constriction member, such that the constriction of the large intestine or urethra is adjusted. Since a relatively small change in the longitudinal extension of the constriction member may result in a relatively large change in the restriction of the intestinal or urethral lumen, the adjustment device may be designed very simple, because the necessary stroke of the displacement between the end portions of the constriction member can be very short.

The adjustment device suitably comprises a movement-transferring member in engagement with at least one of the end portions of the constriction member and operable to displace said one end portion relative to the other end portion of the constriction member. The movement-transferring member may comprise a gear wheel fixed to the other end portion of the constriction member and a gear rack formed on the one end portion of the constriction member, the gear wheel and the gear rack being in mesh with each other. A motor may be connected to the gear wheel and a worm gear may be connected between the motor and the gear wheel. The motor, worm gear, gear wheel and gear rack are suitably contained in a rigid housing that may be at least in part covered with the layer of soft viscoelastic material to protect the large intestine or urethra.

Figure 1:
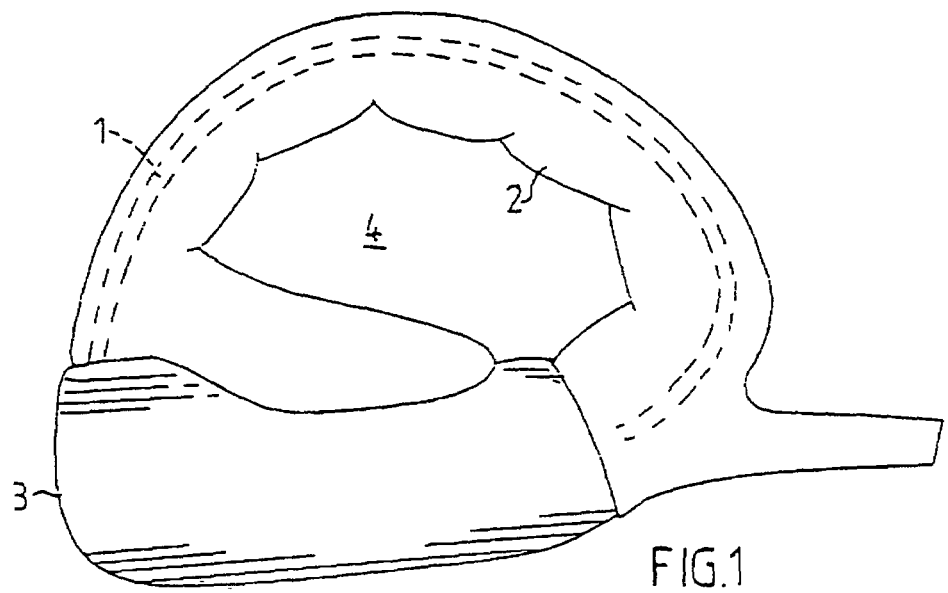
FIG. 1 is a view of an apparatus according to an embodiment of the present invention having a mechanical constriction member in a non-constricted state.

FIG. 1 shows a constriction device of an apparatus of the present invention including an elongated constriction member in the form of a flexible plastic band 1 and a protective layer 2 of a viscoelastic material, such as silicone having hardness less than 20 Shore, applied on the band 1, so that the band 1 is embedded in the protective layer 2. Two end portions of the band 1 are connected to an elongate housing 3 containing an adjustment device, which is capable of establishing longitudinal relative displacement between the end portions. The band 1 and the housing 3 form a closed loop defining a restriction opening 4.

Figure 2:
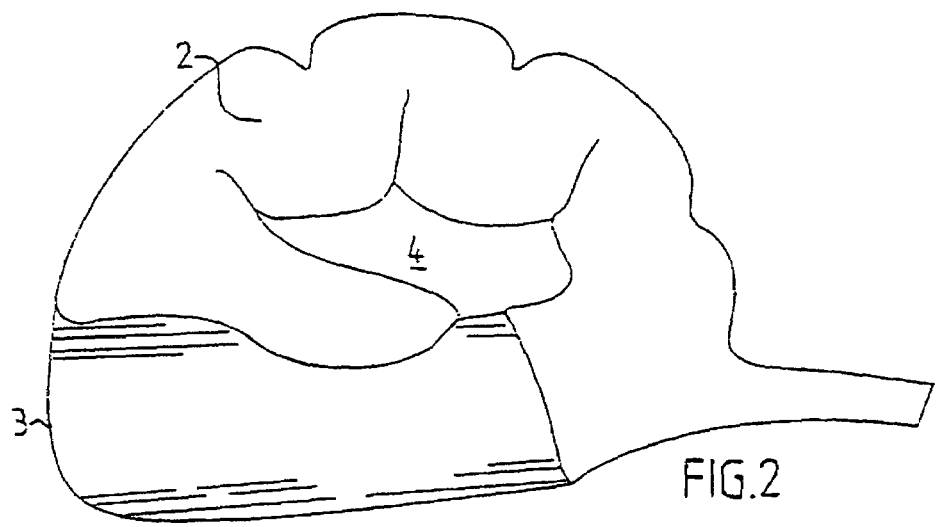
FIG. 2 is a view of the apparatus of FIG. 1 with the constriction member in a constricted state.

FIG. 1 illustrates the apparatus when the restriction opening 4 is relatively large, whereas FIG. 2 illustrates the apparatus when the adjustment device has been operated to pull the end portions together causing the viscoelastic material of the layer 2 to expand inwardly in the loop, so that the restriction opening 4 is reduced. When the constriction device is implanted in an anal incontinent patient, for example with the band 1 applied on the patient's rectum as illustrated in FIG. 4, the restricted cross-sectional area formed in the patient's rectal lumen corresponds to the size of the restriction opening 4.

Figure 3:
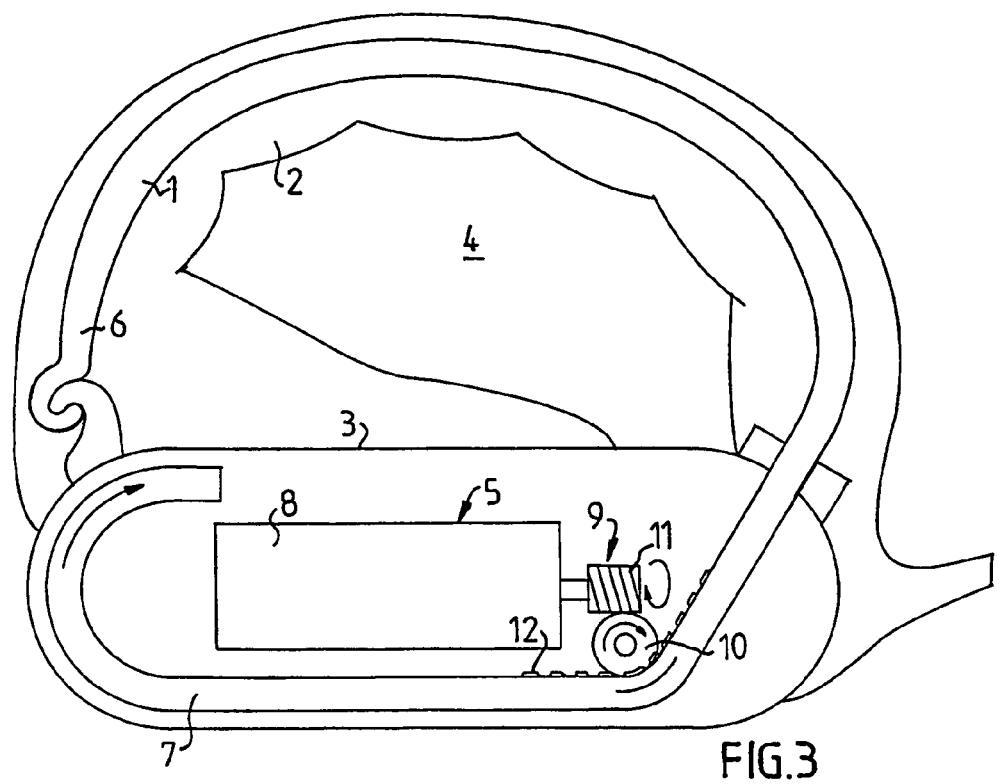
FIG. 3 is a schematic sectional view of the embodiment shown in FIG. 1.

With reference to FIG. 3, the adjustment device 5 will be described in more detail. The band 1 has a first end portion 6 releasably connected to the housing 3 and a second end portion 7 connected to the adjustment device 5. The adjustment device 5 includes an electric motor 8 and a movement transferring means 9 in engagement with the end portion 7. The electric motor 8 operates the movement transferring means 9 to displace the end portion 7 relative to portion 6 in the loop formed by the band 1 and housing 3. The movement-transferring means 9 includes a gear wheel 10 fixed to the housing 3, a worm gear 11 connected between the electric motor 8 and the gear wheel 10, and a gear rack 12 formed on the end portion 7, wherein the gear wheel 10 and the gear rack 12 are in mesh with each other.

Figure 4:
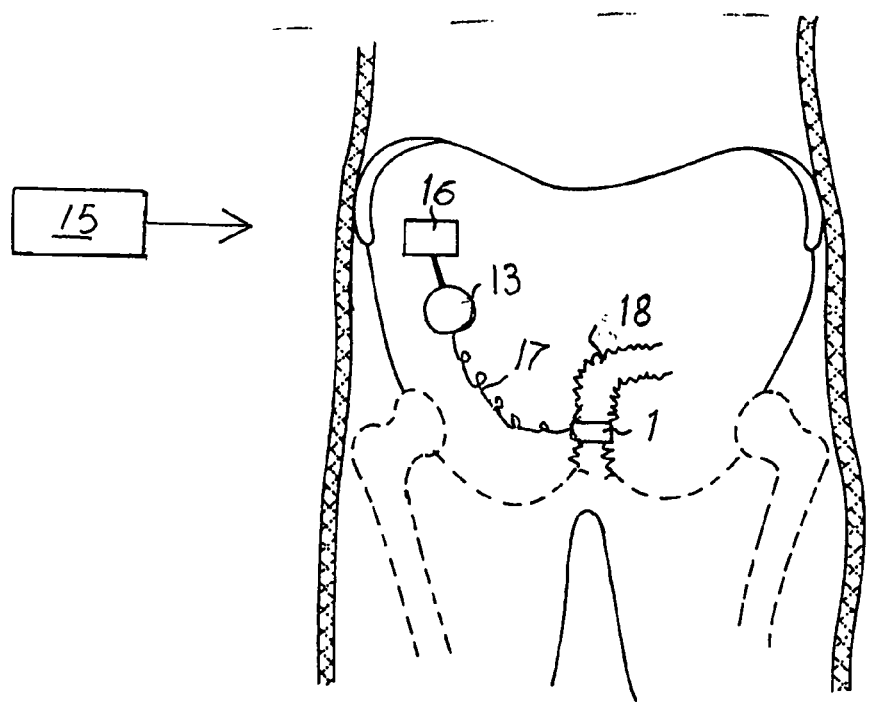
FIG. 4 illustrates the apparatus according to FIGS. 1 and 2 implanted in an anal incontinent patient.

FIG. 4 illustrates the constriction device the embodiment shown in FIGS. 1 and 2 applied on the rectum 18 of an anal incontinent patient. The band 1 and housing 3 of the constriction device extend in a loop around and constricts the rectum to normally close the rectal lumen. A rechargeable electric power supply 13 is implanted in the patient. An external remote control 15 controls the adjustment device 5 and transmits signals that are received by a combined control and energy transforming unit 16 subcutaneously implanted in the patient. The unit 16 is electrically connected to the electric power supply 13 and transforms the energy of the signals into an electric current that is used for charging the electric power supply 13. For example, the signals may include electromagnetic waves and the unit 16 may include an electric p-n junction element that transforms the wireless energy into an electric current.

A resilient insulated electric wire 17 connects the power supply 13 and the electric motor 8 in the housing 3. The electric wire 17 extends helically between the power supply 13 and band 1, in order to permit the electric wire 17 to be temporarily extended when movements of the rectum occur, so that the risk of breaking the electric wire 17 is eliminated.

Figure 5:
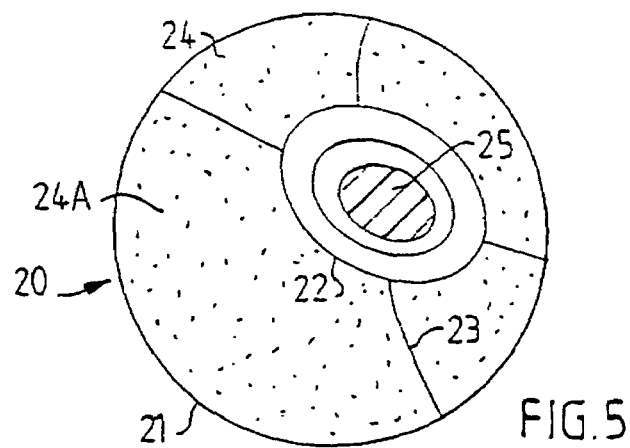
FIG. 5 is a cross-section of a mechanical constriction device according to another embodiment of the invention.

FIG. 5 shows a cross-section of a mechanical constriction device of another embodiment of the invention, comprising a double walled tubing 20, an external wall 21 and an internal wall 22 spaced from the external wall 21. The tubing 20 has partition walls 23 dividing the space between the external and internal walls 21 and 22, respectively, of the tubing 20 into longitudinal cells 24, which are filled with a soft viscoelastic material, such as a gel. A constriction member in the form of a strong band 25 of nylon or the like slides in the tubing 20 to enable adjustment of the constriction device. One cell 24A is larger than the other cells 24 and intended to abut against the large intestine or urethra when the constriction device form a loop around the large intestine or urethra. As a result, when the constriction device is adjusted to constrict the large intestine or urethra, the viscoelastic material located in cell 24A is prevented from flowing to the cells 24 that will be located more or less on the outer side of said loop that does not contact the large intestine or urethra.

The invention claimed is:

1. An apparatus for treating an anal or urinary incontinent patient comprising a constriction device adapted to be applied on the patient's large intestine or urethra, the constriction device including:

an elongate adjustable constriction member adapted to extend in a loop around and constrict the large intestine or urethra, an adjustment device that adjusts the longitudinal extension of the constriction member in the loop to close the intestinal or urethral lumen and release the large intestine or urethra to open the intestinal or urethral lumen, and a layer of a soft material applied on the constriction member, the layer being made of a viscoelastic material of silicone having hardness of less than 20 Shore that is applied on the constriction member, such that the layer is located between the constriction member and the patient's large intestine or urethra at least along a portion of the constriction member, when the constriction device is implanted, to protect the large intestine or urethra from being eroded by the constriction member, the layer of viscoelastic material having an inwardly directed radial extension in said loop, such that when the adjustment device is operated to decrease the longitudinal extension of the constriction member in said loop, the layer of viscoelastic material is forced to expand radially inwardly in the loop so as to have an increased dimension radially inwardly in the loop, causing a corresponding decrease in the cross-sectional area of the intestinal or urethral lumen.

2. An apparatus according to claim 1, wherein the viscoelastic material comprises a foam or gel.

3. An apparatus according to claim 1, wherein the constriction member is non-inflatable.

4. An apparatus according to claim 3, wherein the constriction member comprises a main portion and two elongated end portions, and the adjustment device establishes longitudinal relative displacement between the end portions of the constriction member.

5. An apparatus according to claim 4, wherein the adjustment device comprises a movement transferring means in engagement with at least one of the end portions of the constriction member and operable to displace the one end portion relative to the other end portion of the constriction member.

6. An apparatus according to claim 5, wherein the movement transferring means comprises a gear wheel fixed to the other end portion of the constriction member and a gear rack formed on the one end portion of the constriction member, the gear wheel and the gear rack being in mesh with each other.

7. An apparatus according to claim 6, wherein the adjustment device comprises a motor connected to the gear wheel.

8. An apparatus according to claim 7, wherein the adjustment device comprises a worm gear connected between the motor and the gear wheel.

9. An apparatus according to claim 1 further comprising a rigid housing containing the adjustment device.

10. An apparatus according to claim 1, wherein the adjustment device comprises a motor.

11. An apparatus according to claim 1, wherein the constriction member comprises a hydraulic constriction member and the adjustment device comprises a pump hydraulically connected to the hydraulic constriction member.

12. An apparatus according to claim 1, wherein the adjustment device comprises a powered adjustment device and further comprising an implantable energy transforming device adapted to transform wireless energy emitted from outside the patients body into an energy form suited for powering the adjustment device.

13. An apparatus according to claim 1, further comprising a wireless remote control for controlling the adjustment device to adjust the constriction device.

14. An apparatus according to claim 1, wherein the layer of viscoelastic material has a thickness such that a relatively small change in the longitudinal extension of the constriction member in said loop results in a relatively large change in the restriction of the patient's intestinal or urethral lumen.

* * * * *